(12) United States Patent
Agron et al.

(10) Patent No.: US 7,442,517 B2
(45) Date of Patent: Oct. 28, 2008

(54) **METHOD FOR THE DETECTION OF *SALMONELLA ENTERICA* SEROVAR *ENTERITIDIS***

(75) Inventors: Peter G. Agron, Castro Valley, CA (US); Gary L. Andersen, Berkeley, CA (US); Richard L. Walker, Davis, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 592 days.

(21) Appl. No.: 10/272,715

(22) Filed: Oct. 16, 2002

(65) Prior Publication Data

US 2003/0157696 A1 Aug. 21, 2003

Related U.S. Application Data

(60) Provisional application No. 60/336,089, filed on Oct. 31, 2001.

(51) Int. Cl.
*G01N 33/569* (2006.01)
*G01N 1/68* (2006.01)
*G01N 33/53* (2006.01)
*C12Q 1/00* (2006.01)
*C12Q 1/70* (2006.01)

(52) U.S. Cl. ............................ 435/7.35; 435/4; 435/5; 435/7.1; 435/7.2

(58) Field of Classification Search ............... 435/4, 435/5, 7.2, 7.35, 7.1
See application file for complete search history.

(56) References Cited

U.S. PATENT DOCUMENTS 5,705,365 A * 1/1998 Ryder et al. ............... 435/91.1

OTHER PUBLICATIONS

Agron et al (Abstracts of the General Meeting of the American Society for Microbiology, vol. 101, p. 245, 101st General Meeting of the American Society for Microbiology, Orlando, FL, May 20-24, 2001).*

* cited by examiner

*Primary Examiner*—Vanessa L. Ford
(74) *Attorney, Agent, or Firm*—John H. Lee; Eddie E. Scott; Anne M. Lee

(57) ABSTRACT

Described herein is the identification of a novel *Salmonella enterica* serovar *Enteritidis* locus that serves as a marker for DNA-based identification of this bacterium. In addition, three primer pairs derived from this locus that may be used in a nucleotide detection method to detect the presence of the bacterium are also disclosed her

FIGURE 1A

```
   1 gatccgcttt gcgcctgcga cggcccagac gttattgttt tcagcaacct ggcctgaggc
  61 catcgcggcg attacggtc gtgtacagca gcagccaata cgtattgaaa tcgatacggt
 121 agatgcgcta ccggctatcg aacaacagtt cttcgaaacg tctgcgcatg aaaaaatttc
 181 gctgctacaa acgtgctta gccagcatca gccagcgtcc tgcgtggtat tttgcaatac
 241 caaaaaagat tgtcaggccg tttgtgatgc gcttaatgcg gtaggacaaa gcgcgttggc
 301 gctccacggc gatcggaac aacgcgacg gaaccagacg ttggtgcgtt ttgcaaacgg
 361 tagcgcgcgc attctggttg ccaccgacgt tgccgcgcga ggattagaca ttaaatcgct
 421 cgaactggtg gttaactatg aactggcctg ggacccggag gtgcatgtcc atcgtattgg
 481 cgtacggcg cgcgcggaa gcgcggcct ggcgatcagt ttctgcgcgc cggaagaggc
 541 gcagcgggcg aatattcttt cagaaatgct gcaactcaag ctgaactggc tgaatgcgcc
 601 cgcccgcag cgtcactcc ctctggccgc agagatggct acctatgca ttgacggcgg
 661 caaaaaagcg aaaatgcgtc cgggagatat tttggccgcg ctgaccggcg atattgatt
 721 agacgggcg gatattggca aaattaacgt gcatccaatg cacgtttacg tcgcgtacg
 781 tcaagcagta gcgcaaaaag ctggaagca gttgcaaaac gggaagatca aaggcaagtc
 841 atgcgggta cggctattaa aatgatcgat agcatgcgt ctcaggggag tgctgagacg
 901 cctgcagatt atttcacttc gataacatca agccgacga agcctaaggc ggtgtcatct
 961 tcttccggct gccagccagc gggctgcaag ggaatctctt cacgatcgaa cgctaaatcg
1021 ccgccgtcga cgacctcgga accgtgagtg attccttga aatcgaacag gttagtgtca
1081 caaggtgag acgcacgac atttctgcatg gcgctaaaca tgtctcgat ccgtccagga
1141 tagcgcttat cccagtcgcg tagcatgtcg gcaatcacct gggttgcag gtttggttgc
1201 gaaccgcaca gattacaagg aatgatagg aagctttgg cctcagcaaa acggacaata
1261 tcttctcgc ggcagtaagc cagcgggcg atcacgatat gttgccgtc atcgctcatc
1321 agttcggcg gcatccctt cattttccg cctagaaaca tattcagaaa caggtttgc
1381 agatatcgt cgcaggtgtg ccccagggcg atttggtcg gcccagttc agtcgcgta
1441 cgatacagga tacccgacg caaacgcgag gtaagcggt aagtggtttt tccttccgga
1501 atcttttctt tcacatgcc gtaggtttt tcttcgacga ttttatattc tacgcccagc
1561 tgctcaaggt aggctggcag gatatgttcc ggaaaaccctg gctgcttttg atcgaggttg
1621 acggcgacca gtgaaaaatt gatcggggcg ctttgctgca aattacgtaa aattccagc
1681 atcgtatagc tatctttgcc gccagaaagg caaaccataa tgcgatcgcc ttcttcaatc
1741 atattaaaat cgcaatcgc ttcgccaacg ttaccggcgca ggcgctttg caacttgttg
1801 aggttgtatt gttcctttctt tgtattcttt tgaatttctt gcattttctt agttctctgg
1861 tactaaatgg ggcaaattgg gggcaaactt tgcaactacg ataccgtgc attcaacatc
1921 gctacttgtt cgtcgttcat gtcatcaatc cacatacgt aaatttcata caccatctgc
1981 gcagtttcat gcccattttg gctgcgata aatgccggt tcgctcctgc cgtcaacagc
2041 cagcaggcaa aagtatgtcg cgtattgtat ggattacgt gccgaataca agcagtttt
2101 actgccgcat tccacttgc ccctaaactg cttaccgagt aataggttt ctgtttcct
2161 ttactcatcc tggcatgaa cctgtttcca cttccgcaat accattaaca agttctggat
2221 atagctgttt tcctgttcaa tttcgagaac ctgtggcag ggtaatatgc ctggttgag cgcgggtggc
2281 gtgatgcaaa tatttttgt ctgtggcagc aaacttcgca gtcctgacat atgcaaca cggcgtgtc
2341 gaacggcagg gtggcgacgg cagcgtgtgc cagctcgtc ggccattcc tcgtttttt cgtcgtggc
2401 tgtccgcgtt tcttcggtgc tcttcggtgc cagcgtggc ggatgagcat gggcattcc ccatcttcgc cgcccagctc
2461 gtcagtagcg ggcgtgccgg ggcgtgccgg ggatgagcat aaatgttttg ccatcttcgc cgaagttcgt taacagcggg
2521 atatttctga cagaagtgg tatcaaaact tcctcccgc ggaagttcgt taacagcggg
2581 ggaattaacg cgaaccggtt ttgcaaaatc tgtcggttcg aatccggcgt caagcattga
```

FIGURE 1B

```
2641 tacggcaagg cgtgctgtgg cagcggcttc gctgctttca gttttccacc agaaagcaaa
2701 agggaagccg agacgtttcc gggcgctttc attttaacc ttaatataat atgagtattc
2761 tgttttattg tcgtcatta tcattaccct tattacaaat catacttaat gaagactttc
2821 attttcatt gagcagaatg cgttcgtgac gagctcttta cactccatca gttcaacaa
2881 tgaaataaaa tttcgggag gagcttcgtt cattttaac agcattattg cgctgttat
2941 tgacctgtca tatcgcctg tttcactgtc tgtatatgca acaagagttc tgaaacact
3001 ttcatcgtca cagtccgggg cataagaaac acacagggc atattgttt cgatacataa
3061 cgtacgaatt tttcctgaaa gctggcggag ctctgcaatt actgattcag gtacattttt
3121 catatagatt cctttttca ggttgagtga atcctgcca ttgcagcat atttaaaaac
3181 agatggttt aaacgattac tgttctgtta ccatgattca gctttgcag gcagaccatt
3241 tctgttcagc cagactttta ccatgcaatc gtaatacat cttgcgttg ttaaatcacg
3301 gatataaaa cggcgtttt taatgttatt cgctgaggcg atataagtac gaccatcatg
3361 gataacataa ctctccggcg taatacactg acggtatt tcatccgttc cgaagtgatg
3421 agcaatcata gccctccat ttctgtaa taaattttgt ggtgcggtgc ctgtgcctc
3481 caggtgacat taaccagtta acaattaatg ccgacttaa cattcaccgc tgattcaggg
3541 agtttaact gtgccgcgtg cgcttagccg cattcaccgc atcacaaaat tcactttaaa
3601 aagggcggac atcagaaagg actaagaaaa actgatgccg ccaagtacta cacacagcat
3661 tattgtcgca gtgcaacta caaccggagg cgcacttcca ctattcgat ttacagacaa
3721 gaccgactca gaaaacatca gaaatgcgcc ttcgtgttgt gccggcttt attaaccac
3781 ctccgggctt cgtggctc gctataccc ctacagcgag aacctgtgtt aacatttcaa
3841 taccttaca gttgagagtt attgatatgt cagaaaccgc tctgttatc gtaaaattcc
3901 taattggtaa atccgtcgga caattatgc tcacagtggc tttattttc ttaattatca
3961 tcttcattcc tagagatatt acggagctta ttgaggcgcg tagcgattta ccatatgccg
4021 ttcagattt tagtttgct gtgcttacc ttatagtgct gatcctcaaa gtcactggtt
4081 attttttcgt gtccgcgtg ccgttgtgcc agctaggg caggcaaaa cgcatgttaa
4141 aaacgcttaa ttcattgagt actgaacagc tgttttact tgaaccctt cttaaaactc
4201 attctcccac tttcgggcg tcctgggata acctgatgc agatgctctg gttaaggcag
4261 gtatcgttcg tccgctggt tcgtgtatcg acggtgtttc tgtgatgttc aaaatcgaac
4321 ccgagtatga gtcgttaatg ctttccacct ggaatcccta cacaaaacgg ttcgatatta
4381 gccgttagct gaaagcgcca gcagaaactc actgaaactg agtgcttctt ctcttcgtc
4441 aagcttca aagtattctt cgtaagcctt tccatgatt gtgtcgaaat cctatcact
4501 cacctgagtt tcttctaac cagcgacgtg cgcctgtttc agttttaaac gtcctgcttc
4561 tggtgtacgt catgcggtg aacgttccat cctggtggg gaacacgcca caccaggg
4621 attcgttatt gcgaggtgg atttttgca gcttgtccat tatcacccg gataatactg
4681 ttccgtagt tcgcattgag ctgcaattatc atccaaatac ttgtcgcca atgctggag
4741 agctcgcta aagctgacgt tgcaactatc acgccgggtg gcggaactaa aacctacagc gccgtctgt
4801 catcttccc tctccctta tattagcga tattcataa gtgatcaag ataaatatac atatatca
4861 ttctgagatt atattcga ctatcctaat gaaaataaat gttttatc tgatcaaga gggaggga
4921 taaatatgat ccaaagaaa accgccggga accgcggca gaggcggttg gtcgtcact
4981 ggagctttag gcgcttttgt gcagcgagca tgtttttt cttctcaga agcctcttta tatgctcat
5041 gatttttag tctgaccttt aagccgtca atgagttt tgtctgctca ttcagggagt atatcaaaaa
5101 tctgacctt tctgaccttt aagccgtca atgagttt tgtctgctca ttcagggagt atatcaaaaa
5161 ggttagtaa atcagccctgt tgtctgctca ccattcgcca gcaaccct tcgaagtgt
5221 catcgtaagt accagaagaa cgaacgtagt tcattagatc tcattagatc ggccaaatcc ggtcgtaact
```

FIGURE 1C

```
5281 cttcgggttt aactctcaat agaacagaaa atttttaaggc cgcatcagtg ttgagaggtg
5341 ccttaccgtt caaatagtga ctgacggtag attgtgtctc aaagcccata agatcagcgg
5401 cgatctcctg agtaagtttg aggtctcgct ttttggcgtc ccagatggcg cgtaagcgct
5461 gggtagcttc tggtggagct atttcttcac gtttttttct catgcgctca tcttatgaat
5521 gtgactcata aactcaaact gatataagta ttgatcattt aaattagtat ggttaatatt
5581 tagcgagaat tactaaggtg acctttatga cgttagatga atatttgaaa aaaaatcgtg
5641 tacgacagtc ttgtttggcc acgctggctg gttgttcgca atcgatgatt agccttgtta
5701 ctactggccg tagtcagtta agccccgaaa agtattgcg tatcgcagag gctacgaatt
5761 tcgaggttac acctcatgaa ctccggcctg ataacactta cggagctgag gaggatgacg
5821 gggttaacca tttattcgac ccgccactac ctgacaagg cagaacgttg tgggatgtg
5881 taccaggcgg gcagaagagg ggggatttttc ccgtcagaag aggcttatcg tgcctggaag
5941 aaacaggcga aagtggacgc tgacctgatt tggaagctgc ctgacggtga ggtacgtcgt
6001 tacgacaggc accacaacgt aatttgtcgt gagtgtcgta aaagcgagta catgcagcgg
6061 gtactgcgt tttatcgggg aaactttcag gaggtgctgt tgtgagccaa attaacaatc
6121 ggaactgcgt gaagtgaaag agaaagcata atccaaatat gaataattaa atttagtgat
6181 gtaaataaac tttaatcctt aaccggatgg attcctgcac gctcagaaca ccaggagacc
6241 gcccgaaagg gcggtagctc cattgcttaa ttgtctaaaa tcgtgctaaa tcttttatt
6301 accattaaga aagttatgac agtgataaaa aaggatgtat aggcaaaaa gctaacgata
6361 tatgcgggtg cgcgaaaata ccattttcatt aaatcccactg cattgtcagg caggaaatat
6421 attattactg aaaatataac caatactatt gaagttaata ttgcataagc gacgttgtgg
6481 cataactgct catatatggt tttgttagtg tttaatgata tcaatttgtc tcttgatttg
6541 tttccttcaa ttatatctga tatcttagta atggttttt gtttttgttc ataatcatt
6601 attactgcac tcattaatag tgctgttgta atagccccga agttaacgaa gacggaagca
6661 attgccggtt tcattattcc gtatgtccag cacagaacga aagaaagaga tagaggaact
6721 ataaaatgta cggtaatgtc gctcatcaac attgttccac gctgatctga cattgttttg
6781 tagtgttta ttattacacc cagcacattt atttattca tataatcacc cctttattc
6841 cacagtgcag ttcttccaat atatcattgg aaaggttttt tatcgtgtca tgaagtgctg
6901 ttagatc
```

Figure 2

SEQ ID NO: 2

```
  1 gatctatcct aatgaaaata aatgtgtttt atctgatgca agaggggag ggaggagctt
 61 tagccaaaag aaaaccgccg ggagaggcgg tttgatgtgg ttggttcgtc actgattttt
121 taggcgcttt tgtgcagcga gcatgttctg gaaagcctct ttatatagct cattctgacc
181 tctaagccgg tcaatgagtt tttctttctc agattcaggg agtatatcaa aaaggtttag
241 taaatcagcc tgttgtctgc tcaccattcg ccagccacca ccttcgaagt tgtcatcgta
301 agtaccagaa gaacgaacgt agttcattag atc
```

Figure 3

SEQ ID NO: 3

```
  1 ggccaacagc gtggcgcgaa tatcattcag gataaccgt gcaccgcag cggcaagacc
 61 ctctgcgtag gcaaagccca gtcctcgtgc agaacccgtt accagcgccg ttttcccagt
121 taaatcaaat aaagcggtca tgttgtttcc tcacttgttt aatttgtatg acgactatcc
181 ttttttaggt tgaattttcg ccctgataaa atcaacagtt cacccatgaa tttgcaacaa
241 ggatcacaaa cagctccaca tgccgaccgc gtaattaata ttaattaatt gaattatatg
301 tatatatttg gtttaaattt aacgcagttt gatcgctgtc acagaatggc actcgcagcg
361 atccgctgta aaagaagcgt gatataacag cataaagttg taggacaact tacgtatatc
421 tgttgtatca tccacaacgt tatgacatgc ggtaaattcg ctgagttaag gagtgaaagt
481 gagtaacctg aaaattacca acgtgaaaac gattctgacg gcgccgggcg gcattgattt
541 ggcagtcgtt aagatagaaa ccaacgagcc agggctgtat gggctgggat gtgcgacatt
601 tacccagcgt atcttcgcgg taaaaagcgc gatcgatgag tacatggcgc cttttctggt
661 tggcaaagat ccgacccgta ttgaggacat ctggcggtca ggcgtggtga gcggctactg
721 gcgcaatggc c
```

Figure 4

SEQ ID NO: 4

```
  1 ggccctgcgc tgctgactca cacaggaaat cgacaaagcc ggtaatcagc tcctgttcct
 61 gaggcaggat cgccccgccg atcggagtcc agtaatcgaa accaagctga aggagcttga
121 aaaaacgttt gtggaacgcg tagttacgta ctcgcttaaa atcggcgtgt atccacgcac
181 cgattttac tgagcgcagg aagtcctcac tctccggcgt tgccgggagc agaagccctg
241 atgaggtttg tttaacaagt tgtagatgcg ccatcgttct ctccggtggc gctgtaggtt
301 gctgattgtt caggtcagcc gtaacatatt aaaacattaa taactgacag tgaaacccag
361 tcttatcaga taatcaataa acgcttcaac agacagaatc agatggtcgt caggaattag
421 cgtacagaat gagatttcac cattttttac acgtactgca taaagcccgt cttcatctaa
481 ctctaataaa tccttgagtt ttttcacgtt acctccagac aactaaggaa aaatgaaaag
541 gtgcgatttc aacgcgattc ctgttgaggc gggaaatata aacactgcga ctatttattt
601 cattatataa atttgcttat tttatgttca ccagcaagga catttttcac ttgttgcgca
661 accaatctga aagttgatca tttttatgaa ttttttatttt acgggtaaca aaaaacccgc
721 cgaagcgggt taagtgtggg tgcgttgagg atgcctgaca cgtcagagct ggcggggatt
781 tctccccgc caggtctctt actcctcagg ttcgtaagct gtgaagacag cgacctccgt
841 ctggcc
```

Figure 5

SEQ ID NO: 5    TGTGTTTTATCTGATGCAAGAGG

SEQ ID NO: 8    CGTTCTTCTGGTACTTACGATGAC

Figure 6

SEQ ID NO: 6    GCGAATATCATTCAGGATAAC

SEQ ID NO: 9    GCATGTCATACCGTTGTGGA

Figure 7

SEQ ID NO: 7    GCTGACTCACACAGGAAATCG

SEQ ID NO: 10   TCTGATAAGACTGGGTTTCACT

FIG. 8: Specificity of *Salmonella enterica* serovar Enteritidis detection using the Sdf I primer pair in polymerase chain reactions.

9a: Detection of Sdf I in phage type reference strains.

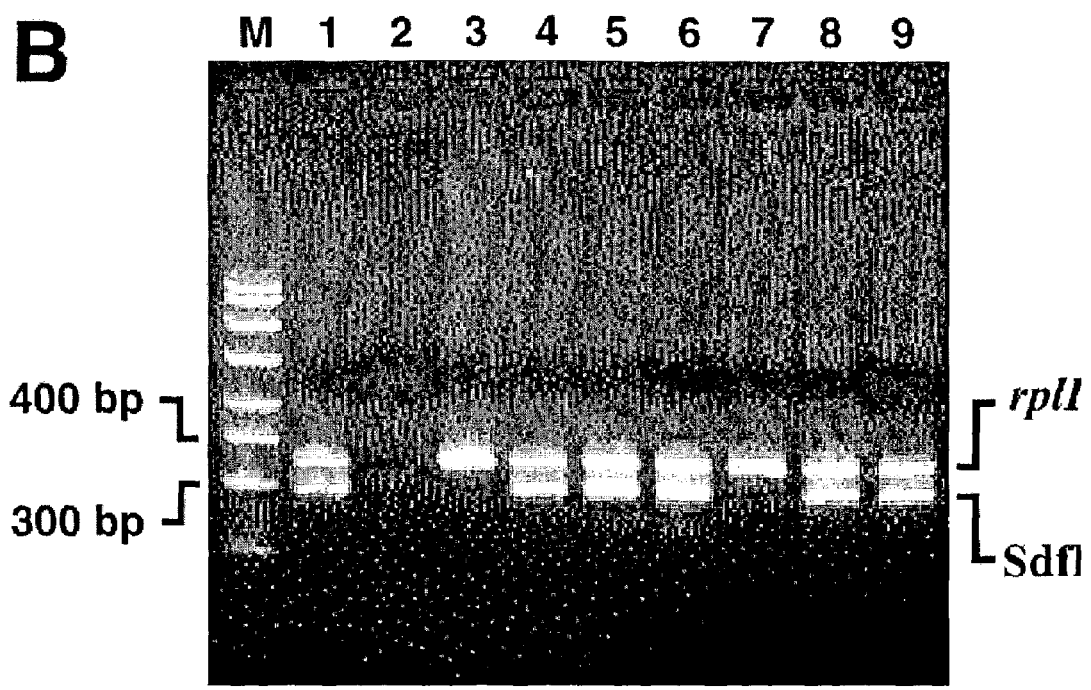
9b: Detection of Sdf I in phage type reference strains and clinical strains of phage types 6A, 6B and 9A.

METHOD FOR THE DETECTION OF SALMONELLA ENTERICA SEROVAR ENTERITIDIS

CROSS-REFERENCE TO RELATED APPLICATIONS

This application claims the benefit of United States Provisional Patent Application No. 60/336,089 filed Oct. 31, 2001 and titled "METHOD FOR THE DETECTION OF *SALMONELLA ENTERICA* SEROVAR *ENTERITIDIS* THAT IS HIGHLY SPECIFIC." United States Provisional Patent Application No. 60/336,089 filed Oct. 31, 2001 and titled "METHOD FOR THE DETECTION OF *SALMONELLA ENTERICA* SEROVAR *ENTERITIDIS* THAT IS HIGHLY SPECIFIC" is incorporated herein by this reference.

The United States Government has rights in this invention pursuant to Contract No. W-7405-ENG-48 between the United States Department of Energy and the University of California for the operation of Lawrence Livermore National Laboratory.

BACKGROUND

In the last few decades, *Salmonella enterica* serovar *Enteritidis* has emerged as a major cause of food-borne illness worldwide. This pathogen is distinguished from its many close relatives also found in poultry environments by its ability to infect chicken ovaries before the eggshell is formed, allowing transmission through intact eggs. Once established in the human host from raw or undercooked eggs or egg products, this bacterium causes gastroenteritis similar to other *Salmonella enterica* serovars. Infection in poultry flocks, which is asymptomatic, was first noticed in the late 1970's, and in the 1980's spread rapidly throughout the United Kingdom, the United States, South America, and other areas. During this period, the proportion of *salmonellosis* cases attributed to *Salmonella* serovar *Enteritidis* increased substantially, showing a 275-fold increase in Argentina and becoming the predominant cause of this disease in the U.S. (see Hogue, A et al. 1997, Epidemiology and control of *Salmonella enteritidis* in the United States of America, Revue Scientifique et Technique 16:542-553, Morales, R. A. et al 1999, Economic Consequences of *Salmonella enterica* Serovar *Enteritidis* Infection in Humans and the U.S. Egg Industry, Iowa State University Press, Ames, Rodrigue, D. C. et al. 1990, International increase in *Salmonella enteritidis*: a new pandemic? Epidemiol. Infect. 105:21-27). Baumler et al. suggested that this rapid increase of *Salmonella* serovar *Enteritidis* may have been due to successful campaigns to eradicate *Salmonella* serovars *Pullorum* and *Gallinarum*, the causative agents in chickens of bacillary white diarrhea and fowl typhoid, respectively ( see Bäumler, A. J., et al. 2000, Tracing the origins of *Salmonella* outbreaks, Science, 287:50-2). It is hypothesized that these avian-adapted *Salmonellae* provided cross-immunity against *Salmonella* serovar *Enteritidis* because of important similarities in lipopolysaccharide structures. Therefore, these campaigns may have opened an ecological niche that has since been occupied by *Salmonella* serovar *Enteritidis*. This view remains controversial, however, as serovars *Gallinarum* and *Pullorum* remain prevalent in many developing countries where serovar *Enteritidis* has nevertheless increased dramatically, and turkey flocks in developed countries, now free of serovars *Gallinarum* and *Pullorum*, have not been colonized by serovar *Enteritidis* (see Pomeroy, B. S. et al. 1991, Fowl typhoid, In: Calnek, B. W., Barnes, H. J., Beard, C. W. et al. [eds.]; Diseases of Poultry. Ames, IA: Iowa State University Press, pp. 100-7, Silva, E. N. 1985, *Salmonella gallinarum* problem in Central and South America. In: Snoyenbos, G. H. [ed], and Proceedings of International Symposium on *Salmonella*, New Orleans, La. American Association of Avian Pathologists, Kennett Square, Pa., pp. 150-6). Unlike the avian-adapted *Salmonellae*, rodents serve as an animal reservoir for *Salmonella* serovar *Enteritidis*, suggesting that culling would not be an effective method of control. It is possible that the use of *Salmonella* serovar *Enteritidis* as a rodenticide may have contributed to the current prevalence of this serovar, and it is also likely that infected rodents are currently a source of disease. In addition to the health risks, this pathogen has had a significant economic impact on the egg industry through decreased consumer confidence following well-publicized outbreaks.

SUMMARY OF THE INVENTION

An aspect of the invention includes a method comprising: providing a sample; providing a DNA sequence, wherein the DNA sequence is complimentary to a target DNA sequence derived from SEQ ID NO: 1, SEQ ID NO: 2, SEQ ID NO: 3, or SEQ ID NO: 4; and detecting the existence of the target DNA sequence by a nucleotide detection method, wherein the existence of the target DNA sequence indicates the presence of *salmonella enterica* serovar *Enteritidis* in the sample.

Another aspect of the invention includes a method comprising: providing a sample; providing at least one primer pair derived from a DNA having a sequence of SEQ ID NO: 1; and detecting *salmonella enterica* serovar *Enteritidis* with PCR.

A further aspect of the invention includes a method comprising: providing a sample; providing at least one primer pair having a sequence of SEQ ID NO: 5 and SEQ ID NO: 8, SEQ ID NO: 6 and SEQ ID NO: 9 or SEQ ID NO: 7 and SEQ ID NO: 10 and detecting *Salmonella enterica* serovar *enteritidis* with PCR.

A further aspect of the invention includes a method comprising: providing a sample; providing an amino acid sequence derived from a DNA sequence consisting of SEQ ID NO: 1, SEQ ID NO: 2, SEQ ID NO: 3, or SEQ ID NO: 4; and detecting *salmonella enterica* serovar *Enteritidis* with PCR.

BRIEF DESCRIPTION OF THE DRAWINGS

FIG. 1A-FIG. 1C shows SEQ ID NO: 1.
FIG. 2 shows SEQ ID NO: 2.
FIG. 3 shows SEQ ID NO: 3.
FIG. 4 shows SEQ ID NO: 4.
FIG. 5 shows SEQ ID NO: 5 and 8.
FIG. 6 shows SEQ ID NO: 6 and 9.
FIG. 7 shows SEQ ID NO: 7 and 10.
FIG. 8 shows an Sdf I amplification product.
FIG. 9a and 9b show the amplification of different phage type reference strains using the Sdf1 primer pair in PCR.

DETAILED DESCRIPTION

Figure 10:
FIG. 10 shows a DNA amplification of the *Salmonella* serovar *Enteritidis* Sdf I region.

*Salmonella enterica* serovar *Enteritidis,* a major cause of food poisoning, can be transmitted to humans through intact chicken eggs when the contents have not been thoroughly cooked. Infection in chickens is asymptomatic; therefore simple, sensitive and specific detection methods can limit human exposure. Described herein is the identification of a novel *Salmonella enterica* serovar *Enteritidis* locus that serves as a marker for DNA-based identification of this bacterium.

Suppression subtractive hybridization (SSH) was used to isolate DNA restriction fragments present in *Salmonella* serovar *Enteritidis*, but absent in other bacteria found in poultry environments. Oligonucleotide primers to candidate regions were used in polymerase chain reactions to test 73 non-*Enteritidis Salmonella enterica* isolates comprising 34 different serovars including *Dublin* and *Pullorum*, two very close relatives of *Enteritidis*. A primer pair to one *Salmonella* difference fragment (Sdf I) clearly distinguished serovar *Enteritidis* from all other serovars tested, while two other primer pairs only identified a few non-*Enteritidis* strains. These primer pairs can also be used to detect a diverse collection of clinical and environmental *Salmonella* serovar *Enteritidis* isolates. In addition, five bacterial genera commonly found with *Salmonella* serovar *Enteritidis* were not detected. Treating total DNA with an exonuclease that degrades sheared chromosomal DNA but not intact circular plasmid DNA, showed that Sdf I is located on the chromosome. The Sdf I primers were used to screen a *Salmonella* serovar *Enteritidis* genomic library and a unique 4060-bp region was defined. This region was used to develop the detection system for *Salmonella* serovar *Enteritidis* described herein. In addition, the 4060-bp region provides sequence information relevant to the unique characteristics of this serovar.

In contrast to other tests, the novel *Salmonella enterica* serovar *Enteritidis* locus described herein is not found in a wide range of closely related serovars including *Dublin* and *Pullorum*, the two closest relatives of *Enteritidis* (see Stanley, J. et al. 1994, Phylogenetics of *Salmonella enteritidis*, International Journal of Food Microbiology. 21:79-87). Thus, the novel *Salmonella enterica* serovar *Enteritidis* locus enables highly specific detection of *Salmonella* serovar *Enteritidis*. The potential problems associated with plasmid-borne markers are circumvented because the locus has a chromosomal location.

An extensive array of *Salmonella* serovar *Enteritidis* phage types from around the world was tested by PCR for the presence of this locus and all phage types associated with human infections were detected. An approximately 7 kb region was isolated by PCR-based screening of a *Salmonella* serovar *Enteritidis* library and subsequently sequenced. A primer pair representing the region of this clone not matching the *Salmonella enterica* serovar *Typhi* or *Paratyphi* complete genomes contains six short open-reading frames. The putative proteins show either weak or no similarity to database sequences. Two other primer pairs were developed that are effective at detecting *Salmonella* serovar *Enteritidis*. The combined use of these primer pairs can provide tools for developing rapid and specific detection methods for *Salmonella enterica* serovar *Enteritidis.*

SUMMARY

The sequence for *Salmonella* difference region I (Sdr I, SEQ ID NO: 1) from *Salmonella enterica* serovar *Enteritidis* CAHFS-285 has been submitted to GENBANK® with accession number AF370716. FIG. 1 shows the sequence of AF370716. Suppression subtractive hybridization was used to find three loci that are restricted to *Salmonella enterica* serovar *Enteritidis* or are found in a few close relatives. The three loci are termed Sdf I (SEQ ID NO: 2), Sdf II (SEQ ID NO: 3) and Sdf III (SEQ ID NO: 4). One region, Sdf I, identified as SEQ ID NO: 2 and depicted in FIG. 2, was only found in serovar *Enteritidis* strains, including a wide range of clinical and environmental samples, and has yielded clear results in laboratory testing. This fact makes this region appropriate for use in the detection of serovar *Enteritidis* within complex samples. Given the wide range of other *Salmonella* serovars and other enteric bacteria found in poultry environments, it is desirable to have markers that will distinguish serovar *Enteritidis* strains from these bacteria. In addition to making an excellent marker for nucleic acid detection, the Sdf I region may also allow the development of an antibody-based test that relies on the detection of one or more putative protein products of the unique ORFs. The extent to which the cloned region varies within serovar *Enteritidis* strains can confirm that other areas of this region are useful for detection purposes. A phage type 8 strain was tested with three primer pairs spanning the unique region (SEQ ID NO: 2) based on the nucleotide sequence from a phage type 4 strain. For this experiment the three primer pairs were designed to correspond to three locations of Sdf I (i.e. SEQ ID NO: 2), to show that the region is similar in different *Enteritidis* isolates, and was not just unique to the strain initially examined. The expected products were observed, indicating that the regions complimentary to the primer pairs were also present in phage type 8 strain. An ongoing project at the University of Illinois to sequence the genome of the phage type 8 strain LK5 can allow for a direct sequence comparison of the Sdf I region from two different phage type strains.

Phage typing is currently the standard method for distinguishing subgroups of serovar *enteritidis* (see Mickman-Brenner, F. W. et al. 1991, Phage typing of *Salmonella enteritidis* in the United States, J. Olin. Microbiol. 29:2817-23, hereby incorporated by reference). This technique was exploited to ensure that a diverse collection of *enteritidis* strains was tested with the diagnostic primer pairs disclosed herein. Using the NVSL reference collection, all of 37 phage types were detected with the Sdf I primer pair (SEQ ID NO: 5, and SEQ ID NO: 8 depicted in FIG. 5) except 6A, 9A, 11,16, 20 and 27. Clinical samples for phage types 11, 16, 20 and 27 are not available, indicating that they are not a significant cause of human infections. Although the phage type 6A and 9A reference strains were not detected with the Sdf I primers, two clinical phage type 9A strains and four clinical phage type 6A strains were unambiguously identified by PCR with the Sdf I primer pair. In summary, the Sdf I primer pair clearly detects all strains of a diverse collection of clinical isolates as well as detecting all environmental isolates tested.

A DNA-based test offers the potential for a significant improvement over current methods of *Salmonella enterica* serovar *Enteritidis* detection. DNA detection offers the possibility of greater speed, sensitivity and ease. The information disclosed herein can be applied to detection in samples taken directly from poultry environments and comparisons can be made to current detection methods. Combined with improved technology, (e.g., see Belgrader, P., et al. 1999, PCR detection of bacteria in seven minutes, Science, 284:449-50), on-site testing can be performed, thus greatly facilitating detection and regular monitoring for serovar *Enteritidis.*

The presence of *Salmonella enterica* serovar *enteritidis* in a sample can be detected using a nucleotide detection method by providing at least one DNA sequence complimentary to a target DNA sequence derived from SEQ ID NO: 1 (Sdr I shown in FIG. 1A-1C), SEQ ID NO: 2 (Sdf I region shown in FIG. 2), SEQ ID NO: 3 (Sdf II region shown in FIG. 3), or SEQ ID NO: 4 (Sdf III region shown in FIG. 4). The presence of *Salmonella enterica* serovar *enteritidis* in a sample can also be detected using polymerase chain reaction (PCR) by providing at least one primer pair derived from SEQ ID NO:1, SEQ ID NO:2, SEQ ID NO:3, or SEQ ID NO:4. For example, the primer pairs SEQ ID NO:5 and SEQ ID NO:8 (shown in FIG. 5), SEQ ID NO:6 and SEQ ID NO:9 (shown in FIG. 6) and SEQ ID NO:7 and SEQ ID NO:10 (shown in FIG. 7) are effective. The nucleotide detection method can comprise microarrays, rolling circle amplification (RCA), Southern Blot, transcription mediated amplification (TMA) or flow cytometery.

PCR is a technique utilized to amplify DNA. Typical PCR reactions include appropriate PCR buffers, DNA polymerase and one or more oligonucleotide primers. Various modifications of PCR techniques are possible as detailed in *Current Protocols in Molecular Biology* ed. F. M. Ausubel, R. Brent, D. D. Moore, K. Struhle, Massachusetts General Hospital and Harvard Medical School (1987) which is hereby incorporated by reference. The following U.S. patents describe PCR and are incorporated herein by reference: U.S. Pat. No. 4,683,195; U.S. Pat. No. 4,683,202; U.S. Pat. No. 4,800,159. The following U.S. patents describe RCA and are incorporated herein by reference: U.S. Pat. No. 6,344,329; U.S. Pat. No. 6,287,824; U.S. Pat. No. 6,210,884; U.S. Pat. No. 6,183,960; and U.S. Pat. No. 5,854,033. The U.S. Pat. No. 5,399,491 describes TMA and is incorporated herein by reference.

DNA microarray, or DNA chips are fabricated by high-speed robotics, generally on glass but sometimes on nylon substrates, for which probes with known identity are used to determine complementary binding, thus allowing massively parallel gene expression and gene discovery studies. An experiment with a single DNA chip can provide researchers information on thousands of genes simultaneously—a dramatic increase in throughput. There are two variants of the DNA microarray technology, in terms of the property of arrayed DNA sequence with known identity: Format I: probe cDNA (500~5,000 bases long) is immobilized to a solid surface such as glass using robot spotting and exposed to a set of targets either separately or in a mixture. This method, "traditionally" called DNA microarray, is widely considered as developed at Stanford University. A recent article by R. Ekins and F. W. Chu (Microarrays: their origins and applications. *Trends in Biotechnology,* 1999, 17, 217-218) seems to provide some generally forgotten facts; Format II: an array of oligonucleotide (20~80-mer oligos) or peptide nucleic acid (PNA) probes is synthesized either in situ (on-chip) or by conventional synthesis followed by on-chip immobilization. The array is exposed to labeled sample DNA, hybridized, and the identity/abundance of complementary sequences is determined. This method, "historically" called DNA chips, was developed at Affimytrix, Inc., which sells its photolithographically fabricated products under the GeneChip® trademark. Many companies are manufacturing oligonucleotide based chips using alternative in-situ synthesis or depositioning technologies. More information on microarrays can be found at the GENE-CHIPS® website.

In one of the embodiment of the invention disclosed herein, Taqman® real time detection may be used for real-time PCR amplification and detection. The principles involved in the conventional Taqman® 5' exonuclease assay are described in detail by Holland et al in, *Detection of specific polymerase chain reaction product by utilizing the 5'—3' exonuclease activity of Thermus aquaticus* DNA polymerase, Proc Natl Acad Sci U S A 88 (16):7276-80, 1991, which is herein incorporated by reference. Taqman® real time detection can also be used to simultaneously detect a plurality of nucleic acid targets when it is used with multiplex PCR, which enables simultaneous detection of more than one target sequence, thus enhancing detection accuracy. Effective target sequences can be derived from DNA sequences SEQ ID NO: 1, SEQ ID NO: 2, SEQ ID NO: 3, or SEQ ID NO: 4. A few examples of typical PCR instruments include the ABI PRISM® 7700, the CEPHEID SMART CYCLER®, and the BIO-RAD ICYCLER™.

Isolation of DNA fragments unique to *Salmonella enterica* serovar *Enteritidis*. Suppression subtractive hybridization (SSH) was used to identify *Salmonella* serovar *Enteritidis*-specific sequences that could serve as diagnostic markers. SSH is a PCR-based technique that enriches for restriction fragments that are present in one strain, termed the tester, but absent in another, termed the driver. *Salmonella* serovar *Enteritidis* strain CAHFS-5 was used as the tester (phage type 8), and the closely related serovar *Dublin* (strain CAHFS-9008117D), also in serogroup D1, was used as the driver. This way, any true SSH products would be likely to distinguish serovar *Enteritidis* from serovar *Dublin* and its close relatives. Four restriction enzymes were used in separate SSH experiments: Rsa I, Alu I, Sau3A I and Hae III. Forty-eight clones from each subtraction (192 total) were sequenced, and PCR primers were synthesized for 98 of the products. Ninety-four clones with high similarity to available non-*Enteritidis* database sequences were not studied further.

PCR amplifications were then performed using the driver and tester DNAs as templates to identify true subtraction products. Nine primer pairs showed amplification with *Salmonella* serovar *Enteritidis* but not with serovar *Dublin.* These unique restriction fragments from which the primers were designed were designated Sdf I to Sdf IX (*Salmonella* difference fragment). One of the nine fragments was from an SSH experiment using Sau3A I (Sdf I), one was an Alu I fragment, five were Hae III fragments (including Sdf II and Sdf III), and two were Rsa I fragments. The primer pairs (referred to as "Sdf I primer pair" etc.) based on these nine sequences were selected for further analysis.

Characterization of DNA fragments unique to *Salmonella* serovar *Enteritidis*. The nine primer pairs that amplified sequences from *Salmonella* serovar *Enteritidis* but not serovar *Dublin* were PCR tested with several other serovars commonly found in the poultry environment to eliminate those primer pairs that were not serovar *Enteritidis*-specific. Amplification of sequences from one isolate each of *Salmonella* serovars *Typhimurium, Heidelberg, Montevideo,* and another isolate of *Salmonella* serovar *Enteritidis* (CAHFS-285, a phage type 4 strain) were used for this purpose. In addition, the two strains used in the subtraction (*Salmonella* serovar *Dublin* CAHFS-9008117D and *Salmonella* serovar *Enteritidis* CAHFS-5) were included as controls. Three of the nine primer pairs detected both strains of serovar *Enteritidis* but none of the other serovars. These three primer pairs were further evaluated using an extensive collection of *Salmonella enterica* serovars available at the CAHFS. Eighty-one additional *S. enterica* isolates were then tested, including 30 additional serovars (for a total of 34 non-*Enteritidis* serovars including those described above, Table 1) and 12 additional serovar *Enteritidis* environmental and poultry isolates (Table 2). Most of the 34 non-*Enteritidis* serovars are encountered at egg production facilities and therefore complicate diagnostic efforts to detect serovar *Enteritidis.*

The SDf II primer pair (SEQ ID NO: 60 and SEQ ID NO:8 identified seven of the 73 non-*Enteritidis* isolates, representing sic non-*Enteritidis* serovars. One of the strains was an isolate of *Salmonella* serovar *dublin,* even though this primer pair does not detect the strain of serovar *Dublin* used for the substraction experiments. This primer pair detected one isolate of *Salmonella* serovar *Worthington,* while another isolate of the same serovar was not detected, indicating that there is some degree of diversity within serovars that can be detected by primers form SSH experiments. It is not known if theses differences are due to nucleotide differences in 3' end of primer-binding site, or whether larger differences are responsible.

Another primer pair, to Sdf III (SEQ ID NO: 7 and SEQ ID NO: 10), amplified a specific product of the predicted size only with the serovar *Enteritidis* isolates, but amplified other products in six non-*Enteritidis* isolates (serovars *Lomalinda, Mbandaka, Blockley, Derby, Reading* and *Kentucky*) and produced a smear with one isolate (serovar *Berta*). Clear positive results were obtained with all 14 serovar *Enteritidis* environmental, poultry and other animal isolates tested in this panel (Table 2). The third primer pair that was tested with this panel of strains was the Sdf I primer pair, which yielded remarkably clear results. No products were amplified from the 73 non-*Enteritidis* isolates, but all 14 serovar *Enteritidis* isolates showed a clear band of the expected size.

FIG. 8 shows an Sdf I amplification product for three of the most common phage types of *Salmonella* serovar *Enteritidis* (lanes 3-5), while four other *Salmonella* serovars found in the poultry environment do not show this amplicon (lanes 6-9). Referring to FIG. 8, Lane M, size standards; lane 1, *Salmonella* serovar *Enteritidis* CAHFS-546 (phage type 8); lane 2, no template; lane 3, *Salmonella* serovar *Enteritidis* CAHFS-184 (phage type 4); lane 4, *Salmonella* serovar *Enteritidis* 97-6371A (phage type 8); lane 5, *Salmonella* serovar *Enteritidis* 97-1866IN (phage type 13A); lane 6, *Salmonella* serovar *Pullorum*; lane 7, *Salmonella* serovar *Typhimurium*; lane 8, *Salmonella* serovar *Heidelberg;* lane 9, *Salmonella* serovar *Montevideo;* lane 10, *Escherichia coli*; lane 11, *Citrobacter freundii*. Amplicons produced by the Sdf I primers (293 bp) and the rplI primers (343 bp) are indicated. In addition, two other enteric bacteria, *Escherichia coli* ATCC 25922 and *Citrobacter freundii* ATCC 43864 (lanes 10 and 11) are not detected with this primer pair. The Sdf I primer pair was also tested with other bacteria common in poultry environments, namely *Proteus mirabilis* ATCC 33946, *Proteus vulgaris* ATCC 13315, *Enterobacter aerogenes* ATCC 13048, *Enterobacter cloacae* ATCC 13047, and *Providencia rettgeri* ATCC 29944, and did not show any amplification.

The Sdf I, Sdf II and Sdf III primer pairs were then used to test 37 NVSL phage type reference strains of *Salmonella* serovar *Enteritidis* (Table 3). The Sdf I sequence was present in all but 6 of 37 phage types (PTs 6A, 9A, 11, 16, 20 and 27). No clinical isolates for phage types 11, 16, 20, and 27 are available from the Centers for Disease Control and Prevention (B. Holland, personal communication) suggesting that infections from these phage types are exceedingly rare. A subset of these data is presented in FIG. 9a. Amplification of 12 different phage types is shown, with only phage type 6A (lane 7) and 9A (lane 10) showing negative results. Referring to FIG. 9a, Lane M, size markers; lane 1, CAHFS-546 (positive control); lane 2, no template; lane 3, phage type 2; lane 4, phage type 3; lane 5, phage type 4; lane 6, phage type 6; lane 7, phage type 6A; lane 8, phage type 8; lane 9, phage type 9; lane 10, phage type 9A; lane 11, phage type 13A; lane 12, 95-13141 (phage type 14B); lane 13, phage type 24; lane 14, phage type 34. FIG. 9b shows the detection of Sdf I in phage type reference strains and clinical strains of phage types 6A, 6B and 9A. Lane M, size markers; lane 1, CAHFS-546 (positive control); lane 2, no template; lane 3, NVSL 9 (phage type 6A); lane 4, CAHFS-435 (phage type 6A); lane 5, CAHFS-436 (phage type 6A); lane 6, CAHFS-739 (phage type 6B); lane 7, NVSL 13 (phage type 9A); lane 8, D0144-CDC (phage type 9A); lane 9, D01760-CDC (phage type 9A). Amplicons produced by the Sdf I primers (293 bp) and rplI primers (343 bp) are indicated.

Although these results suggest that the Sdf I primers cannot detect other isolates of phage type 6A or 9A, two clinical isolates of phage type 6A (lanes 4 and 5 of FIG. 9b) and phage type 9A (FIG. 9b, lanes 8 and 9) are readily detected with the Sdf I primer pair. Four additional isolates of phage type 6A were also tested, and were detected with the Sdf I primers (Table 2). In addition, one isolate of phage type 6B was also detected (FIG. 9b, lane 6). These results suggest that strains that are clearly infectious are detected with the Sdf I primers.

The Sdf I and Sdf III primers showed the same pattern when tested with the NVSL strains except for the NVSL phage type 40 reference strain, raising the possibility that the Sdf I and Sdf III difference fragments may be linked in the *Salmonella* serovar *Enteritidis* genome. One difference between the Sdf I and Sdf III primer pairs is that the Sdf III primers generate other products for several of the templates that are not the expected size. The Sdf II primer pair showed amplification with all 37 phage types.

The three primer pairs were also tested against 10 additional serovar *Enteritidis* clinical isolates taken from stool samples of afflicted humans (Table 2). Eight were phage type 4, one was phage type 7, and one was phage type 13. These 10 samples are geographically diverse, having been collected in Spain, Italy, Mexico, and across the United States from Connecticut to Hawaii. All three primer pairs detected the 10 strains.

Combined with the testing of the phage type 6A, 6B and 9A strains discussed above, 16 clinical isolates were tested, and all were detected with the Sdf I primers. Thus, one highly specific marker for *Salmonella* serovar *Enteritidis* (Sdf I) has been developed, as well as two other markers that are useful for narrowing *Salmonella enterica* to just a few serovars.

Database searches with the sequences of Sdf I (333 bp), Sdf II (731 bp) and Sdf III (846 bp) showed that positions 5-274 of Sdf III, when translated, showed high similarity to the deduced amino acid sequence of a hypothetical protein of the putative cryptic phage CP-933R of *E. coli* O157:H7 strain EDL933 (E value $4 \times 10^{-39}$). Sdf I and Sdf II showed no similarity to database sequences.

Chromosomal localization of the Sdf I locus. To determine if the Sdf I marker is located on the chromosome or located on a circular plasmid, we developed the following novel assay (FIG. 10). Referring to FIG. 10, the *Salmonella* serovar *Enteritidis* Sdf I region is located on the chromosome. Lane 1, total DNA amplified with rplI primers (343-bp amplicon). Lane 2, total DNA amplified with the Sdf I primers (293-bp amplicon). Lane 3, total DNA amplified with the spvC primers (565-bp amplicon). Lane 4, plasmid preparation treated with exo-DNase amplified with rplI primers. Lane 5, plasmid preparation treated with exo-DNase and amplified with Sdf I primers. Lane 6, plasmid preparation treated with exo-DNase and amplified with spvC primers. Lanes 7, 8, 9 are the same as lanes 4, 5, 6, respectively, but without exo-DNase treatment before amplification. Strain CAHFS-285 (phage type 4) was used for these experiments.

A commercially available exodeoxyribonuclease was used to treat plasmid preparations of *Salmonella* serovar *Enteritidis* CAHFS-285, a phage type 4 isolate. The enzyme digests contaminating chromosomal DNA present in all plasmid preparations, but does not affect covalently closed or nicked circular DNAs, i.e. circular plasmids. In addition to the Sdf I primer pair, a primer pair to a known chromosomal gene encoding the L9 ribosomal protein (rplI), and a primer pair to a known *Salmonella* plasmid-borne gene, spvC, were used as controls. Lanes 1-3 show that these primer pairs readily amplify products from total cellular DNA. As expected, all three amplicons were observed in the untreated plasmid preparations (lanes 7-9). In exonuclease treated samples, however, the spvC product (lane 6) showed significant amplification, whereas the rplI (lane 4) and the Sdf I (lane 5) products were only faintly visible. Because the Sdf I signal was reduced similarly to a known chromosomal sequence, this suggests that Sdf I is located on the chromosome.

Figure 11:
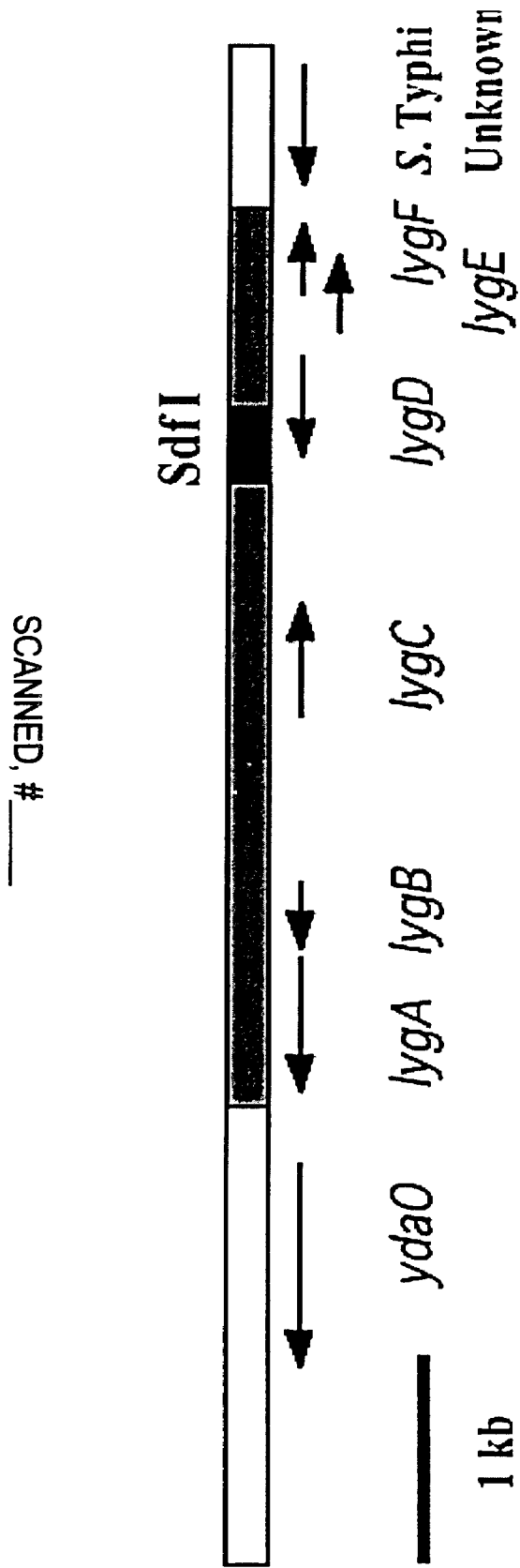
FIG. 11 shows the chromosomal context of Sdf I.

Cloning of the Sdf I locus. To define the region of the chromosome containing the 333 bp Sdf I SSH product (*Salmonella* difference region I), a library was constructed using total DNA from the phage type 4 *Salmonella* serovar *Enteritidis* strain CAHFS-285. A total of 6,528 *E. coli* colonies containing plasmids with 4-6 kb inserts, representing greater than 99% of the cellular DNA (assuming a genome size of 5 megabase pairs), were screened by PCR in pools using the Sdf I primer pair. One clone was identified and the complete sequence of its 6,907 bp insert was determined (FIG. 11). Referring to FIG. 11, a schematic representation of the Sdf I region from *Salmonella* serovar *Enteritidis* CAHFS-285 (phage type 4). Open boxes indicate sequence with identity to *Salmonella enterica* serovar *Typhi*. Gray and black indicate novel sequence. Sdf I, bounded by Sau3A I sites, is shown in black. All open-reading frames greater than 100 codons are indicated with black arrows. There was no similarity to the sequence of Sdf III, which was detected in a similar pattern to that of Sdf I. Sdf I, a Sau3A I fragment isolated by SSH, is found between positions 4928 and 5260 of the genomic clone (black region of FIG. 11). Nucleotide sequence comparisons with database sequences showed a near perfect match at each end to the complete *Salmonella enterica* serovar *Typhi* genome. On the left end as shown, the match extends from position 1 to position 2101, and on the right end from position 6160 to 6907. On the left end is a copy of a gene with near-perfect identity to the *E. coli* ydaO gene. The matches were to two widely separated regions of the serovar *Typhi* genome (1361375 to 1363475 on the left, 1920934 to 1920189 on the right), suggesting that this region is the site of a major rearrangement with respect to serovar *Enteritidis*. Overlapping PCR amplifications were used to confirm that the 6,907-bp region of the library clone is contiguous in *Salmonella* serovar *Enteritidis* and not the result of the ligation of two or more unrelated fragments (data not shown). There are six open-reading frames greater than 100 codons in the 4060 bp novel region (gray and black bars in FIG. 11). We have designated these six ORFs, lygA-F, for linked to the ydaO gene. These six open reading frames encode possible proteins of 207, 105, 173, 155, 119, and 110 amino acids for lygA-F, respectively. Using a protein BLAST search of the non-redundant database, LygA (position 2161-2784) shows similarity to Exonuclease VIII of *Salmonella* serovar *Typhimurium* (E value $2 \times 10^{-8}$). LygC (position 3867-4388) exhibits weak similarity to phage superinfection exclusion protein B of *E. coli* (E value $6 \times 10^{-5}$), while LygD (position 5036-5503) shows even weaker similarity to phage λ repressor cI (E value $1 \times 10^{-4}$). LygF shows some similarity to a hypothetical protein of prophage CP-933R of *E. coli* O157:H7, an enterohemorrhagic strain (E value $1 \times 10^{-22}$). LygE and F overlap to a large extent, which may indicate that one, the other, or both are not genes. The deduced amino acid sequences of lygB and lygE do not show any similarity to database sequences with a protein BLAST search.

Amplification by PCR was used to examine other areas of the unique region defined by comparison to *Salmonella* serovar *Typhi*. Primer pairs to lygA, lygC and lygD were used to amplify sequences from a *Salmonella* serovar *Enteritidis* phage type 8 strain (CAHFS-546), and a *Salmonella* serovar *Dublin* strain (CAHFS-9008117D), as well as the library strain, *Salmonella* serovar *Enteritidis* CAHFS-285 as a positive control. Products of the expected size were observed in the *Enteritidis* strains, but not the Dublin strain, consistent with the view that the entire unique region is present in *Enteritidis*strains, but absent in Dublin strains (data not shown). When primers to the non-unique flanking sequences, which would generate an approximately 4.5 kb amplicon in serovar *Enteritidis* strains comprising the unique region were used with the serovar *Dublin* strain mentioned above, an approximately 600 bp product was observed. This may indicate that all or most of the unique region is missing in serovar *Dublin,* and the locus is otherwise collinear. Sequencing the 600-bp amplicon will help to define the precise nature of the difference between the two serovars.

Materials and Methods

Strains. Strains used are listed in Tables 1, 2 and 3. Some strains, as indicated in the text, were obtained from the American Type Culture Collection (ATCC), Rockville, Md. Serotyping was verified or performed by the California Animal Health and Food Safety Laboratory (CAHFS) using standard procedures. The National Veterinary Services Laboratory (NVSL), Ames, Iowa, performed phage typing by standard methods (see Hickman-Brenner, F. W. et al. 1991, Phage typing of *Salmonella enteritidis* in the United States. J. Clin. Microbiol. 29:2817-23).

DNA preparation. DNA was isolated from 3 ml cultures after overnight growth in Luria Bertani medium (Sigma, St. Louis, Mo.). Either of two methods was used to purify total DNA, both of which yielded consistent results. DNA STAT-60 isolation reagent (Tel-Test, Friendswood, Tex.) was used according to the manufacturer's recommendations (1 ml per culture). Alternatively, cell pellets were resuspended in 200 µl of TE buffer (10 mM Tris HCl, 1 mM EDTA pH 8.0), and treated with 2.5 µg/ml proteinase K for 30 minutes at 37° C. Successive extractions were performed with saturated phenol, phenol:chloroform, (1:1 v/v) and chloroform:isoamyl alcohol (24:1 v/v). DNA was precipitated with 0.5 ml cold 95% ethanol and 75 µl 3 M sodium acetate pH 5.2, dried under vacuum in a desiccator and resuspended in water.

DNA amplification for strain testing. Oligonucleotide primers (Sigma-Genosys, The Woodlands, Tex.) at 400 nM final concentration were combined with 200 pg genomic DNA template and amplified with Advantage 2 Polymerase (ClonTech, Palo Alto, Calif.). After an initial denaturation at 94° C. for 1 minute, the samples were subjected to 27 cycles of 94° C. for 30s, 58° C. for 30s, and 72° C. for 1 min, followed by a final 7 minute 72° C. incubation. Samples were fractionated by 2% agarose gel electrophoresis and visualized by ethidium bromide staining. A primer pair to either the 23S or 16S rRNA gene was used as a positive control for the amplification of each DNA sample, or a primer pair to the rplI gene (encoding the L9 ribosomal protein) was used as an internal control.

Suppression subtraction hybridization, DNA sequencing and analysis. Genome comparisons by suppression subtraction hybridization were performed essentially as described by Akopyants et al. (see Akopyants, N. S. et al. 1998, PCR-based subtractive hybridization and differences in gene content among strains of *Helicobacter pylori*, Proc. Natl. Acad. Sci. 95:13108-13, hereby incorporated by reference) with the following exceptions: For subtractions with Sau3A I digested DNA, adaptor 1 was formed by annealing the adaptor 1 long oligonucleotide with the oligonucleotide 5' GATCACCTGC-CCGG (SEQ ID NO: 11) to form an adaptor with appropriate cohesive ends. Similarly, adaptor 2 was formed by annealing the adaptor 2 long oligonucleotide with the oligonucleotide 5' GATCCAATCGGCCG (SEQ ID NO: 12). Ligase (New England Biolabs, Beverly, Mass.) was inactivated by incubation at 72 degrees for 20 minutes. Unpurified PCR products were cloned using the pGEM® T-Easy TA cloning kit (Promega, Madison, Wis.). Recombinant clones were picked using a BioRobotics (Woburn, Mass.) BIOPICK™ automated colony picker, and plasmid templates were prepared by boiling lysis and magnetic bead capture using a high-throughput procedure (see Skowronski, E. W. et al. 2000, Magnetic, microplate-format plasmid isolation protocol for high-yield, sequencing-grade DNA. Biotechniques, 29:786-792, hereby incorporated by reference). Sequencing of plasmid templates was performed using the Applied Biosystems (Foster City, Calif.) Big-Dye™ Terminator system and either ABI PRISM® 377 or 3700 automated sequencers. The sequencing primers used were 5' TGTAAAACGACGGCCAGT (SEQ ID NO: 13) (forward) and 5' CAGGAAACAGCTATGACC (SEQ ID NO: 14) (reverse). Sequences were assembled and oligonucleotide primers were designed using the Consed software package (U. Washington, Seattle). Sequence comparisons with the GENBANK® databases were performed using the BLAST (basic local alignment search tool) server at the Baylor College of Medicine (Houston, Tex.) or the server at the National Center for Biotechnology Information (Bethesda, Md.). Both the non-redundant and the unfinished microbial databases were used for comparisons.

Oligonucleotide primers. Sequences of the primer pairs used (Sigma-Genosys, The Woodlands, Tex.) for DNA amplification are as follows: spvC, 5'

```
spvC,       5' CTCTGCATTTCACCACCATCACG and
            (SEQ ID NO: 15)

5' CTTGCACAACCAAATGCGGAAGAT;
            (SEQ ID NO: 16)

rpll,       5' GGGTGATCAGGTTAACGTTAAAG and
            (SEQ ID NO: 17)

5' CTTCGTGTTCGCCAGTGGTACGC;
            (SEQ ID NO: 18)

23S,        5' CTACCTTAGGACCGTTATAGTTAC and
            (SEQ ID NO: 19)

5' GAAGGAACTAGGCAAAATGGTGCC;
            (SEQ ID NO: 20)

16S,        5' AGAGTTTGATCCTGGCTCAG and
            (SEQ ID NO: 21)

5' GGTTACCTTGTTACGACTT;
            (SEQ ID NO: 22)

Sdf I,      5' TGTGTTTTATCTGATGCAAGAGG and
            (SEQ ID NO: 23)

5' CGTTCTTCTGGTACTTACGATGAC;
            (SEQ ID NO: 24)

Sdf II,     5' GCGAATATCATTCAGGATAAC and
            (SEQ ID NO: 25)

5' GCATGTCATACCGTTGTGGA;
            (SEQ ID NO: 26)

Sdf III,    5' GCTGACTCACACAGGAAATCG and
            (SEQ ID NO: 27)

5' TCTGATAAGACTGGGTTTCACT.
            (SEQ ID NO: 28)
```

Deoxyribonuclease assays. Plasmids were prepared from Salmonella serovar Enteritidis CAHFS-285, by a standard alkaline lysis method (see Birnboim, H. C. et al. 1979, A rapid alkaline extraction procedure for screening recombinant plasmid DNA. Nucl. Acids Res. 7:1513-1523, hereby incorporated by reference) except that proteins and cell debris were precipitated with 7.5 M ammonium acetate (½ volume) instead of sodium acetate. The DNA from a 10 ml culture was resuspended in 40 µl of TE, and 10 µl was digested with PLASMID-SAFE™ DNase (Epicentre Technologies, Madison, Wis.) in a 250 µl reaction with 50 units of enzyme for 5 hours according to the manufacturer's recommendations. Five µl of this reaction were used as a template in PCRs (30 cycles, 1 minute annealing at 65° C., 1 minute extension at 72° C., 30 second denaturation at 94° C.).

Library construction and screening. To construct a genomic library of Salmonella serovar Enteritidis strain CAHFS-285, 100 µg of total DNA was partially digested with 100 units Sau3A I (New England Biolabs, Beverly, Mass.) for 10 minutes. The DNA was fractionated by electrophoresis, and 4-6 kb fragments were excised and gel purified by electroelution. These fragments were ligated to pUC9 (see Vieira, J. et al. 1982, The pUC plasmids, an M13mp7-derived system for insertion mutagenesis and sequencing with synthetic universal primers, Gene 19:259-68, hereby incorporated by reference) that had been digested with Barn HI (New England Biolabs, Beverly Mass.), gel purified and treated with shrimp alkaline phosphatase (US Biochemicals, Cleveland, Ohio). Products were introduced into Escherichia coli DH10B cells (Gibco BRL, Rockville, Md.) by electroporation (GENE-PULSER®, BIORAD™, Richmond, Calif.) and transformants were selected with 50 µg/ml ampicillin (Sigma, St. Louis, Mo.) on agar plates with Luria Bertani (LB) medium. Using a BIOPICK™ automated colony picker, white colonies (6,528) were used to inoculate 384-well microfiter plates (Nalge Nunc, Rochester, N.Y.) containing LB with 7.5% (v/v) glycerol, followed by overnight incubation at 37° C. The library was replicated using a 384-pin tool and stored at 70° C. Screening was performed using the Sdf I primers by amplification of combined cultures followed by amplification of single cultures. For each row, 5 µl of each culture was combined and 1 µl of the mixture was PCR tested. For rows with a positive signal, the individual clones were then tested. One clone consistently yielded positive results in PCRs and was selected for sequencing.

DNA sequencing of the Sdf I region. The library clone identified by PCR with the Sdf I primers was purified by alkaline lysis and anion exchange chromatography using a Qiagen (Valencia, Calif.) Plasmid Preparation Kit. The plasmid DNA was digested with Eco RI and Hind III, separated by electrophoresis, and the two insert fragments were gel purified using a Qiaex II kit (Qiagen). The purified fragments were first treated with the Kienow fragment of DNA polymerase I (New England Biolabs) and deoxynucleoside triphosphates, followed by digestion with Alu I, Hae III and Rsa I in separate reactions. Then the products from each of the 3 reactions were separately cloned into pPA9 that had been digested with Eco RV and treated with shrimp alkaline phosphatase. The plasmid pPA9 was constructed by annealing the oligonucleotides 5' AGCTTGGAATTCGATATCAGGC-CTCG (SEO ID NO: 29) and 5' GATCCGAGGCCT-GATATCGAATTCCA (SEO ID NO: 30) which were then cloned between the Hind III and Barn HI sites of pUC9 (see Vieira, J. et al. 1982, The pUC plasmids, an M13mp7-derived system for insertion mutagenesis and sequencing with synthetic universal primers, Gene 19:259-68, hereby incorporated by reference). Thirty-two clones from each enzyme sublibrary (96 total) were sequenced as described above and overlapping sequences were assembled with the Consed program to generate the complete sequence of the insert. The assembly was corroborated with restriction mapping based on the sequence.

Nucleotide sequence accession numbers. The sequences for *Salmonella* difference fragments (Sdf) I-IX from *Salmonella enterica* serovar *Enteritidis* CAHFS-5 have been submitted to GENBANK® with accession numbers AF370707-15, respectively. The sequence for *Salmonella* difference region I (Sdr I) from *Salmonella enterica* serovar *Enteritidis* CAHFS-285 has been submitted to GENBANK® with accession number AF370716. FIG. 1A-1C shows the sequence of AF370716.

The invention claimed is:

1. A method of indicating the presence of *Salmonella enterica* serovar *enteritidis* in a sample comprising the steps of:
providing the sample, wherein the sample contains or does not contain a target DNA sequence SEQ ID NO: 1, or a target DNA sequence SEQ ID NO: 2, or a target DNA sequence SEQ ID NO: 3, or a target DNA sequence SEQ ID NO: 4;
adding primers to the sample, wherein said primers bind to said target DNA sequence SEQ ID NO: 1, or target DNA sequence SEQ ID NO: 2, or target DNA sequence SEQ ID NO: 3, or target DNA sequence SEQ ID NO: 4;
amplifying said target DNA sequence SEQ ID NO: 1, or target DNA sequence SEQ ID NO: 2, or target DNA sequence SEQ ID NO: 3, or target DNA sequence SEQ ID NO: 4 that include said bound primers; and
detecting the existence of said target DNA sequence SEQ ID NO: 1, or target DNA sequence SEQ ID NO: 2, or target DNA sequence SEQ ID NO: 3, or target DNA sequence SEQ ID NO: 4 by a nucleotide detection method, wherein the existence of said target DNA sequence SEQ ID NO: 1, or target DNA sequence SEQ ID NO: 2, or target DNA sequence SEQ ID NO: 3, or target DNA sequence SEQ ID NO: 4 indicates the presence of *Salmonella enterica* serovar *enteritidis* in the sample.

2. The method recited in claim 1, wherein said nucleotide detection method comprises micro-arrays.

3. The method recited in claim 1, wherein said nucleotide detection method comprises rolling circle amplification (RCA).

4. The method recited in claim 1, wherein said nucleotide detection method comprises Southern blot.

5. The method of indicating the presence of *Salmonella enterica* serovar *enteritidis* in a sample recited in claim 1, wherein said step of detecting the existence of the target DNA sequence by a nucleotide detection method comprises Transcription Mediated Amplification (TMA).

6. The method recited in claim 1, wherein said nucleotide detection method comprises flow cytometery.

7. The method recited in claim 1, wherein said nucleotide detection method includes a PCR detection method that comprises real-time PCR.

8. The method recited in claim 7, wherein said primer pair has the sequence of SEQ ID NO: 5 and SEQ ID NO:8 or SEQ ID NO: 6 and SEQ ID NO:9 or SEQ ID NO: 7 and SEQ ID NO:10.

9. A method of indicating the presence of *Salmonella enterica* serovar *enteritidis* in a sample comprising the steps of:
providing the sample, wherein the sample contains or does not contain a target DNA sequence SEQ ID NO: 1, or a target DNA sequence SEQ ID NO: 2, or a target DNA sequence SEQ ID NO: 3;
adding a primer pair to the sample, wherein said primer pair binds to said target DNA sequence SEQ ID NO: 1, or said target DNA sequence SEQ ID NO: 2, or said target DNA sequence SEQ ID NO: 3,
said primer pair has the sequence of SEQ ID NO: 5 and SEQ ID NO:8 or SEQ ID NO: 6 and SEQ ID NO:9 or SEQ ID NO: 7 and SEQ ID NO:10;
amplifying said target DNA sequence SEQ ID NO: 1, or said target DNA sequence SEQ ID NO: 2, or said target DNA sequence SEQ ID NO: 3 that include said bound primer pair; and
detecting the existence of said target DNA sequence SEQ ID NO: 1, or said target DNA sequence SEQ ID NO: 2, or said target DNA sequence SEQ ID NO: 3, wherein the existence of said target DNA sequence SEQ ID NO: 1, or said target DNA sequence SEQ ID NO: 2, or said target DNA sequence SEQ ID NO: 3 indicates the presence of *Salmonella enterica* serovar *enteritidis* in the sample.

10. The method recited in claim 9, wherein the step of amplifying said target DNA sequence SEQ ID NO: 1, or said target DNA sequence SEQ ID NO: 2, or said target DNA sequence SEQ ID NO: 3 that include said bound primer pair is accomplished using real-time PCR.

11. A method of indicating the presence of *Salmonella enterica* serovar *enteritidis* in a sample comprising the steps of:
providing the sample, wherein the sample contains or does not contain a target DNA sequence SEQ ID NO: 1, or a target DNA sequence SEQ ID NO: 2, or a target DNA sequence SEQ ID NO: 3, or a target DNA sequence SEQ ID NO: 4;

adding a primer pair to the sample, wherein said primer pair bind to said target DNA sequence SEQ ID NO: 1, or said target DNA sequence SEQ ID NO: 2, or said target DNA sequence SEQ ID NO: 3, or said target DNA sequence SEQ ID NO: 4;

said primer pair has the sequence of SEQ ID NO: 5 and SEQ ID NO:8 or SEQ ID NO: 6 and SEQ ID NO:9 or SEQ ID NO: 7 and SEQ ID NO:10;

amplifying said target DNA sequence SEQ ID NO: 1, or said target DNA sequence SEQ ID NO: 2, or said target DNA sequence SEQ ID NO: 3, or said target DNA sequence SEQ ID NO: 4; and detecting the existence of said target DNA sequence SEQ ID NO: 1, or said target DNA sequence SEQ ID NO: 2, or said target DNA sequence SEQ ID NO: 3, or said target DNA sequence SEQ ID NO: 4, by a nucleotide detection method, wherein the existence of said target DNA sequence SEQ ID NO: 1, or said target DNA sequence SEQ ID NO: 2, or said target DNA sequence SEQ ID NO: 3, or said target DNA sequence SEQ ID NO: 4 indicates the presence of *Salmonella enterica* serovar *enteritidis* in the sample.

* * * * *

```
                              SEQUENCE LISTING

<160> NUMBER OF SEQ ID NOS: 10

<210> SEQ ID NO 1
<211> LENGTH: 6907
<212> TYPE: DNA
<213> ORGANISM: Salmonella enterica

<400> SEQUENCE: 1
gatccgcttt gcgcctgcga cgcgccagac gttattgttt tcagcaacct ggcctgaggc      60
catcgcggcg attagcggtc gtgtacagca gcagccaata cgtattgaaa tcgatacggt     120
agatgcgcta ccggctatcg aacaacagtt cttcgaaacg tctgcgcatg aaaaaatttc     180
gctgctacaa acgttgctta gccagcatca gccagcgtcc tgcgtggtat tttgcaatac     240
caaaaaagat tgtcaggccg tttgtgatgc gcttaatgcg gtaggacaaa gcgcgttggc     300
gctccacggc gatctggaac aacgcgaccg cgaccagacg ttggtgcgtt ttgcaaacgg     360
tagcgcgcgc attctggttg ccaccgacgt tgccgcgcga ggattagaca ttaaatcgct     420
cgaactggtg gttaactatg aactggcctg ggacccggag gtgcatgtcc atcgtattgg     480
ccgtacggcg cgcgcgggaa gcagcggcct ggcgatcagt ttctgcgcgc cggaagaggc     540
gcagcgggcg aatattcttt cagaaatgct gcaactcaag ctgaactggc tgaatgcgcc     600
cgcccggcag ccgtcactcc ctctggccgc agagatggct accctatgca ttgacggcgg     660
caaaaaagcg aaaatgcgtc cgggagatat tttgggcgcg ctgaccggcg atattggatt     720
agacggggcg gatattggca aaattaacgt gcatccaatg cacgtttacg tcgccgtacg     780
tcaagcagta gcgcaaaaag cctggaagca gttgcaaaac gggaagatca aaggcaagtc     840
atgccgggta cggctattaa aatgatcgat agcatggcgt ctcagcggag tgctgagacg     900
cctgcagatt atttcacttc gataacatca agccgcaacg cctctaaggc ggtgtcatct     960
tcttccggct gccagccagc gggctgcaag ggaatctctt cacgatcgaa cgctaaatcg    1020
ccgccgtcga cgacctcgga accgtgagtg attcctttga aatcgaacag gttagtgtca    1080
caaaggtgag acggcacgac attctgcatg gcgctaaaca tcgtctcgat ccgtccagga    1140
tagcgcttat cccagtcgcg tagcatgtcg gcaatcacct ggcgttgcag gtttggttgc    1200
gaaccgcaca gattacaagg aatgataggg aaggctttgg cctcagcaaa acggacaata    1260
tctttctcgc ggcagtaagc cagcgggcgg atcacgatat gtttgccgtc atcgctcatc    1320
agtttcggcg gcatcccttt catttttccg ccatagaaca tattcagaaa cagggtttgc    1380
agaatatcgt cgcgatggtg gcccagggcg attttggtcg cgcccagttc agtcgccgta    1440
cgatacagga taccccgacg caaacgcgag cacagcgagc aggtggtttt tccttccgga    1500
atcttttctt tcacaatgcc gtaggtgttt tcttcgacga ttttatattc tacgcccagc    1560
tgctcaaggt aggctggcag gatatgttcc ggaaaacctg gctgcttttg atcgaggttg    1620
acggcgacca gtgaaaaatt gatcggggcg ctttgctgca aattacgtaa aatttccagc    1680
atcgtatagc tatctttgcc gccagaaagg caaaccataa tgcgatcgcc ttcttcaatc    1740
```

```
atattaaaat cggcaatcgc ttcgccaacg ttacggcgca ggcgcttttg caacttgttg    1800
aggttgtatt gttctttctt tgtattcttt tgaatttctt gcattatttc agttctctgg    1860
tactaaatgg ggcaaattgg gggcaaactt tgcaactacg ataaccgtgc attcaacatc    1920
gctacttgtt cgtcgttcat gtcatcaatc cacataccgt aaatttcata caccatctgc    1980
gcagtttcat gccccatttg gctggcgata aatgccgggt tcgctcctgc cgtcaacagc    2040
cagcaggcaa aagtatgtcg cgtatggtac ggattacggc ggcgaatacc agcacgtttt    2100
actgccgcat tccaccttgc ccctaaactg cttaccgagt aataaggttt ctgttttcct    2160
ttactcatcc tgggcatgaa cctgttcaga cttccgcaat accattaaca ggttctggat    2220
atagctgttt tcctgttcca tttcgagaac ggtaatatgc ctgcgttgag cgcgggtggc    2280
gtgatgcaaa tatttttgt ctgtggcagc gtaagtaaaa atgtgcaaca cgcgctgggg    2340
gaacggcagg gtggcgacgg aaacttcgca gtcctgacat tcgtcgttgt cactggtgtc    2400
tgtcccgctt tcttcggtgc cagcgtcgtc ggcgcattcc tccgttttt cgtcgtgggc    2460 gtcagtagcg ggcgtgccgg ggatgagcat aaatgttttg ccatcttcgc cgcccagctc    2520
atatttctga cagaaggtgg tatcaaaact tccctccggc ggaagttcgt taacagcggg    2580
ggaattaacg cgaaccggtt ttgcaaaatc tgtcggttcg aatccggcgt caagcattga    2640
tacggcaagg cgtgctgtgg cagcggcttc gctgctttca gttttccacc agaaagcaaa    2700
agggaagccg agacgtttcc gggcgctttc atttttaacc ttaatataat atgagtattc    2760
tgttttattg tcgctcatta tcattaccct tattacaaat catacttaat gaagactttc    2820 attttcatt gagcagaatg cgttcgtgac gagctcttta cactccatca gtttcaacaa    2880
tgaaataaaa ttttcgggag gagcttcgtt cattttaac agcattattg cggctgttat    2940
tgacctgtca tatgcgcctg tttcactgtc tgtatatgca acaagagttc tggaaacact    3000
ttcatcgtca cagtcccggg cataagaaac aacacagggc atattgtttt cgatacataa    3060
cgtacgaatt tttcctgaaa gctggcggag ctctgcaatt actgattcag gtacattttt    3120
catatagatt cctttttca ggttgagtga attcctgcca ttgcaggcat atttaaaaac    3180
aggatggttt aaacgattac tgttctgtta ccatgattca gctttggcag gcagaccatt    3240
tctgttcagc cagactttta ccatgcaatc ggtaatacat ctttgcgttg ttaaatcacg    3300
gatatataaa cggcgttttt taatgttatt cgctgaggcg atataagtac gaccatcatg    3360
gataacataa tctcccggcg taatacactg acgcggtatt tcatccgttc cgaagtgatg    3420
agcaatcata gccccctccat ttctggtaaa taaattttgt ggtgcggtgc ctggtgcctc    3480
caggtgacat taaccagtta acaattaatg ccgacttaaa ccacccatac tgattcaggg    3540
agttttaact gtgccgcgtg cgcttagccg cattcaccgc atcacaaaat tcactttaaa    3600
aagggcggac atcagaaagg actaagaaaa actgatgccg ccaagtacta cacacagcat    3660
tattgtcgca gtggcaacta caaccggagg cgcacttcca ctatttggat ttacagacaa    3720
gaccgactca gaaaacatca gaaatgcgcc ttcgtgttgt gcccggcttt atttaaccac    3780
ctccgggctt cggtggtctc ggctataccc ctacagcgag aacctgtgtt aacatttcaa    3840 taccccttaca gttgagagtt attgatatgt cagaaaccgc tctggttatc gtaaaattcc    3900
taattggtaa atccgtcgga caattttatgc tcacagtggc tttattttc ttaattatca    3960 tcttcattcc tagagatatt acggagctta ttgaggcgcg tagcgattta ccatatgccg    4020
ttcagatttt tagttttgct gtggcttacc ttatagtgct gatcctcaaa gtcactggtt    4080
attttttcgt gtcggcgctg ccgttgtgcc agcgtagggg cagggcaaaa cgcatgttaa    4140
```

```
aaacgcttaa ttcattgagt actgaacagc tgtttttact tgaacccttt cttaaaactc    4200
attctcccac tttccgggcg tcctgggata accctgatgc agatgctctg gttaaggcag    4260
gtatcgttcg tccggctggt tcgtgtatcg acggtgtttc tgtgatgttc aaaatcgaac    4320
ccgagtatga gtcgttaatg cttttccacct ggaatccctg cacaaaacgg ttcgatatta   4380
gccgttagct gaaagcgcca gcagaaactc actgaaactg agtgcttctt ctccttcgtc    4440
aaggctttca agtattctt cgtaagcctt ttccatgatt gtgtcgaaat ccatatcact     4500
cacctgagtt tctttctaac cagcgacgtg cgcctgtttc agttttaaac gtcctgcttc    4560
tggtgtacgt catggcggtg aacgttccat cctggttggg gaacacgcca cacaccaggg    4620
attcgttatt gccgaggtgg attttttgca gcttgtccat tatcaccccg gataatactg    4680
ttcctgtagc tcgcattgag ccaaaaacat atcccatcca ttgtcgcgca atgcttggag    4740
agctgcgcta agctgacgt tgcaactatc catcaaatac tgaatcactt cattccttcc     4800
catctttccc tctccccta acgccgggtg gcggaactaa aacctacagc gccgtgctgt     4860
ttctgagatt atattagcga tattcatata gttgatcaag ataaatatac atatatatca    4920
taaatatgat ctatcctaat gaaaataaat gtgttttatc tgatgcaaga gggggaggga    4980
ggagctttag ccaaaagaaa accgccggga gaggcggttt gatgtggttg gttcgtcact    5040
gattttttag gcgcttttgt gcagcgagca tgttctggaa agcctcttta tatagctcat    5100
tctgaccttt aagccggtca atgagttttt ctttctcaga ttcagggagt atatcaaaaa    5160
ggtttagtaa atcagcctgt tgtctgctca ccattcgcca gccaccacct tcgaagttgt    5220
catcgtaagt accagaagaa cgaacgtagt tcattagatc ggccaaatcc ggtcgtaact    5280
cttcgggttt aactctcaat agaacagaaa attttaaggc cgcatcagtg ttgagaggtg    5340
ccttaccgtt caaatagtga ctgacggtag attgtgtctc aaagcccata agatcagcgg    5400
cgatctcctg agtaagtttg aggtctcgct ttttggcgtc ccagatggcg cgtaagcgct    5460
gggtagcttc tggtggagct atttcttcac gttttttct catgcgctca tcttatgaat     5520
gtgactcata aactcaaact gatataagta ttgatcattt aaattagtat ggttaatatt    5580
tagcgagaat tactaaggtg acctttatga cgttagatga atatttgaaa aaaaatcgtg    5640
tacgacagtc ttgtttggcc acgctggctg gttgttcgca atcgatgatt agccttgtta    5700
ctactggccg tagtcagtta agccccgaaa aggtattgcg tatcgcagag gctacgaatt    5760
tcgaggttac acctcatgaa ctccggcctg ataacactta cggagctgag gaggatgacg    5820
gggttaacca tttattcgac ccgccactac ctggacaagg cagaacgttg tggggatgtg    5880
taccaggcgg gcagaagagg ggggattttc ccgtcagaag aggcttatcg tgcctggaag    5940
aaacaggcga agtggacgc tgacctgatt tggaagctgc ctgacggtga ggtacgtcgt     6000
tacgacaggc accacaacgt aatttgtcgt gagtgtcgta aaagcgagta catgcagcgg    6060
gtactggcgt tttatcgggg aaactttcag gaggtgctgt tgtgagccaa attaacaatc    6120
ggaactgcgt gaagtgaaag agaaagcata atccaaatat gaataattaa atttagtgat    6180
gtaaataaac tttaatcctt aaccggatgg attcctgcac gctcagaaca ccaggagacc    6240
gcccgaaagg gcggtagctc cattgcttaa ttgtctaaaa tcgtgctaaa tcttttatt     6300 accattaaga aagttatgac agtgataaaa aaggatgtat aggctaaaaa gctaacgata    6360
tatgcgggtg cgcgaaaata ccatttcatt aaatccactg cattgtcagg caggaaatat    6420
attattactg aaaatataac caatactatt gaagttaata ttgcataagc gacgttgtgg    6480
```

```
cataactgct catatatggt tttgttagtg tttaatgata tcaatttgtc tcttgatttg    6540
tttccttcaa ttatatctga tatcttagta atggtttttt gttttttgttc ataaatcatt   6600 attactgcac tcattaatag tgctgttgta atagccccga agttaacgaa gacggaagca    6660
attgccggtt tcattattcc gtatgtccag cacagaacga agaaagaga tagaggaact     6720 ataaaatgta cggtaatgtc gctcatcaac attgttccac gctgatctga cattgttttg   6780
tagtgtttta ttattacacc cagcacattt attttattca tataatcacc cctttatttc   6840
cacagtgcag ttcttccaat atatcattgg aaaggttttt tatcgtgtca tgaagtgctg   6900
ttagatc                                                              6907

<210> SEQ ID NO 2
<211> LENGTH: 333
<212> TYPE: DNA
<213> ORGANISM: Salmonella enterica

<400> SEQUENCE: 2
gatctatcct aatgaaaata aatgtgtttt atctgatgca agaggggag ggaggagctt     60 tagccaaaag aaaaccgccg ggagaggcgg tttgatgtgg ttggttcgtc actgattttt   120
taggcgcttt tgtgcagcga gcatgttctg gaaagcctct ttatatagct cattctgacc   180
tctaagccgg tcaatgagtt tttctttctc agattcaggg agtatatcaa aaaggtttag   240
taaatcagcc tgttgtctgc tcaccattcg ccagccacca ccttcgaagt tgtcatcgta   300
agtaccagaa gaacgaacgt agttcattag atc                                333

<210> SEQ ID NO 3
<211> LENGTH: 731
<212> TYPE: DNA
<213> ORGANISM: Salmonella enterica

<400> SEQUENCE: 3
ggccaacagc gtggcgcgaa tatcattcag gataacccgt gcacccgcag cggcaagacc     60
ctctgcgtag gcaaagccca gtcctcgtgc agaacccgtt accagcgccg ttttcccagt   120
taaatcaaat aaagcggtca tgttgtttcc tcacttgttt aatttgtatg acgactatcc   180
ttttttaggt tgaattttcg ccctgataaa atcaacagtt cacccatgaa tttgcaacaa   240
ggatcacaaa cagctccaca tgccgaccgc gtaattaata ttaattaatt gaattatatg   300
tatatatttg gtttaaattt aacgcagttt gatcgctgtc acagaatggc actcgcagcg   360
atccgctgta aagaagcgt gatataacag cataaagttg taggacaact tacgtatatc    420
tgttgtatca tccacaacgg tatgacatgc ggtaaattcg ctgagttaag gagtgaaagt   480
gagtaacctg aaaattacca acgtgaaaac gattctgacg gcgccgggcg gcattgattt   540
ggcagtcgtt aagatagaaa ccaacgagcc agggctgtat gggctgggat gtgcgacatt   600
tacccagcgt atcttcgcgg taaaaagcgc gatcgatgag tacatggcgc ttttctggt    660 tggcaaagat ccgacccgta ttgaggacat ctggcggtca ggcgtggtga gcggctactg   720
gcgcaatggc c                                                         731

<210> SEQ ID NO 4
<211> LENGTH: 846
<212> TYPE: DNA
<213> ORGANISM: Salmonella enterica

<400> SEQUENCE: 4
ggccctgcgc tgctgactca cacaggaaat cgacaaagcc ggtaatcagc tcctgttcct     60
```

```
gaggcaggat cgccccgccg atcggagtcc agtaatcgaa accaagctga aggagcttga      120
aaaaacgttt gtggaacgcg tagttacgta ctcgcttaaa atcggcgtgt atccacgcac      180 cgattttac tgagcgcagg aagtcctcac tctccggcgt tgccgggagc agaagccctg       240
atgaggtttg tttaacaagt tgtagatgcg ccatcgttct ctccggtggc gctgtaggtt      300
gctgattgtt caggtcagcc gtaacatatt aaaacattaa taactgacag tgaaacccag      360
tcttatcaga taatcaataa acgcttcaac agacagaatc agatggtcgt caggaattag      420
cgtacagaat gagatttcac catttttac acgtactgca taaagcccgt cttcatctaa       480
ctctaataaa tccttgagtt ttttcacgtt acctccagac aactaaggaa aaatgaaaag      540
gtgcgatttc aacgcgattt ctgttgaggc gggaaatata acactgcga ctatttattt       600 cattatataa atttgcttat tttatgttca ccagcaagga cattttcac ttgttgcgca       660 accaatctga aagttgatca tttttatgaa ttttatttt acgggtaaca aaaaacccgc       720
cgaagcgggt taagtgtggg tgcgttgagg atgcctgaca cgtcagagct ggcggggatt      780 tctccccgc caggtctctt actcctcagg ttcgtaagct gtgaagacag cgacctccgt       840
ctggcc                                                                 846
```

```
<210> SEQ ID NO 5
<211> LENGTH: 23
<212> TYPE: DNA
<213> ORGANISM: Artificial Sequence
<220> FEATURE:
<223> OTHER INFORMATION: Forward Primer

<400> SEQUENCE: 5
tgtgttttat ctgatgcaag agg                                              23

<210> SEQ ID NO 6
<211> LENGTH: 24
<212> TYPE: DNA
<213> ORGANISM: Artificial Sequence
<220> FEATURE:
<223> OTHER INFORMATION: Reverse Primer

<400> SEQUENCE: 6
cgttcttctg gtacttacga tgac                                             24

<210> SEQ ID NO 7
<211> LENGTH: 21
<212> TYPE: DNA
<213> ORGANISM: Artificial Sequence
<220> FEATURE:
<223> OTHER INFORMATION: Forward Primer

<400> SEQUENCE: 7
gcgaatatca ttcaggataa c                                                21

<210> SEQ ID NO 8
<211> LENGTH: 20
<212> TYPE: DNA
<213> ORGANISM: Artificial Sequence
<220> FEATURE:
<223> OTHER INFORMATION: Reverse Primer

<400> SEQUENCE: 8
gcatgtcata ccgttgtgga                                                  20

<210> SEQ ID NO 9
```

-continued

```
<211> LENGTH: 21
<212> TYPE: DNA
<213> ORGANISM: Artificial Sequence
<220> FEATURE:
<223> OTHER INFORMATION: Forward Primer

<400> SEQUENCE: 9
gctgactcac acaggaaatc g                                              21

<210> SEQ ID NO 10
<211> LENGTH: 22
<212> TYPE: DNA
<213> ORGANISM: Artificial Sequence
<220> FEATURE:
<223> OTHER INFORMATION: Reverse Primer

<400> SEQUENCE: 10
tctgataaga ctgggtttca ct                                             22
```